(12) United States Patent
Lloyd

(10) Patent No.: US 6,479,694 B1
(45) Date of Patent: Nov. 12, 2002

(54) PREPARATION OF CHIRAL CIS-5-AMINO-2-CYCLOPENTEN-1-OL DERIVATIVES

(75) Inventor: Michael Lloyd, Cambridge (GB)

(73) Assignee: Chirotech Technology, Ltd. (GB)

( * ) Notice: Subject to any disclaimer, the term of this patent is extended or adjusted under 35 U.S.C. 154(b) by 0 days.

(21) Appl. No.: 09/890,946

(22) PCT Filed: Feb. 24, 2000

(86) PCT No.: PCT/GB00/00648

§ 371 (c)(1),
(2), (4) Date: Aug. 7, 2001

(87) PCT Pub. No.: WO00/50412

PCT Pub. Date: Aug. 31, 2000

(30) Foreign Application Priority Data

Feb. 25, 1999 (GB) .............................................. 9904377

(51) Int. Cl.$^7$ ..................... C07C 261/00; C07C 205/00; C07C 69/74
(52) U.S. Cl. ........................ 560/115; 560/125; 560/128
(58) Field of Search ................................ 560/115, 125, 560/128

(56) References Cited

PUBLICATIONS

Muxworthy et al, Tetrahedron Letters vol. 36, No. 41, pp 7539–7540.*

Anderson, Glen T., et al., "Studies on Total Synthesis of the Cytotoxic Marine Alkaloid Agelastatin A", *J. Org. Chem.*, Oct. 13, 1998, pp. 7594–7595, vol. 63, American Chemical Society, "Published on Web".

Maier, Martin E., "Synthesis of Cyclohexenylamines by Ring Closing Metathesis", *SYNLETT*, Aug. 1998, pp. 891–893.

Mulvihill, Mark J. et al., "Enzymatic Resolution of Aminocyclopentenols as Precursors to D– and L–Carbocyclic Nucleosides," *J. Org. Chem.*, Apr. 28, 1998, pp. 3357–3363, vol. 63, American Chemical Society, "Published on Web".

Muxworthy, James P., et al., "Stereoselective Cycloadditions of Chiral Acyl–Nitroso Compounds; Unexpected Formation of an Oxazolidinone," *Tetrahedron Letters*, 1995, pp. 7539–7540, vol. 36, No. 41; Elsevier Science Ltd., printed in Great Britain.

\* cited by examiner

*Primary Examiner*—Alan L. Rotman
*Assistant Examiner*—Hector M Reyes
(74) *Attorney, Agent, or Firm*—Saliwanchik, Lloyd & Saliwanchik

(57) ABSTRACT

As process for the preparation of a cyclic carbamate of formula (1), comprises treatment of a cyclopentene of formula (2) wherein $R^1$ is H or an organic group of up to 20 C atoms and $R^2$ is $C_{1-10}$ alkyl, aralkyl or aryl, with a source of halogen and a base.

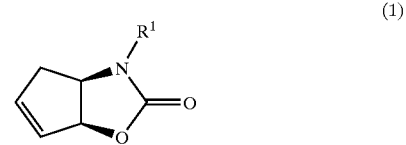

(1)

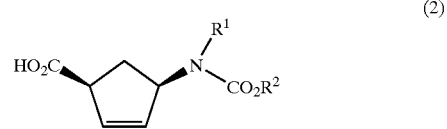

(2)

21 Claims, No Drawings

PREPARATION OF CHIRAL CIS-5-AMINO-2-CYCLOPENTEN-1-OL DERIVATIVES

This application is a National Stage Application of International Application Number PCT/GB00/00/00648, published, pursuant to PCT Article 21(2), in English.

FIELD OF THE INVENTION

This invention relates to a process for the production of chiral cis-5-amino-2-cyclopenten-1-ol as its cyclic carbamate.

BACKGROUND TO THE INVENTION cis-5-Amino-2-cyclopenten-1-ol is an extremely useful synthon, especially in the form of derivatives such as the cyclic carbamate 1 (3,3a,4,6a-tetrahydro-cyclopentaoxazol-2-one). For example, conversion of 1 to N-Boc derivative gives an intermediate which is a suitable substrate for $Pd^0$-catalysed nucleophilic allylic displacement (Muxworthy et al., *Tetrahedron Letters*, 1995, 36, 7539–7540), as shown in the following Scheme.

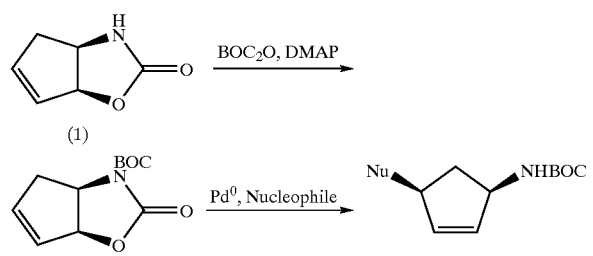

This reaction was demonstrated for 2 model nucleophiles. Products of such reactions establish 1,3-chiral centres on the cyclopentane ring. This structural motif is an important synthetic target, particularly for elaboration into carbocyclic nucleosides and analogues of nucleoside derivatives, reviewed for example by Agrofoglio et al. (*Tetrahedron*, 1994, 50, 10611–10670).

As further demonstration of the synthetic utility of the N-Boc derivative of compound 1, Anderson et al. (*J. Org. Chem.*, 1998, 63, 7594–7595) report diastereoselective allylic amination reactions.

Synthesis of the cyclic carbamate 1 represents a challenge, especially when it is required in the form of a single enantiomer. Two syntheses of the latter have been reported. In the earlier of these, Muxworthy et al. (as above) used a mandelic acid derivative to introduce chirality. Thus an acyl nitroso intermediate, generated in situ from (R)-α-hydroxyphenylacetohydroxamic acid, undergoes a Diels-Alder reaction with cyclopentadiene, and the resulting adduct is treated with HCl to effect rearrangement to give a salt derivative of cis-5-amino-2-cyclopenten-1-ol. Further treatment with either $Et_3N/TsCl$ or t-BuOK/PhNTf$_2$ yields 1 in modest yield (30–35%) and requires chromatographic purification. Overall, this route appears impractical to operate at scale, because of the extremely low temperature required in the initial cycloaddition. In addition, a stoichiometric amount of the expensive (R)-mandelic acid is required as chiral auxiliary, recovery and reuse of which is precluded by its mode of removal.

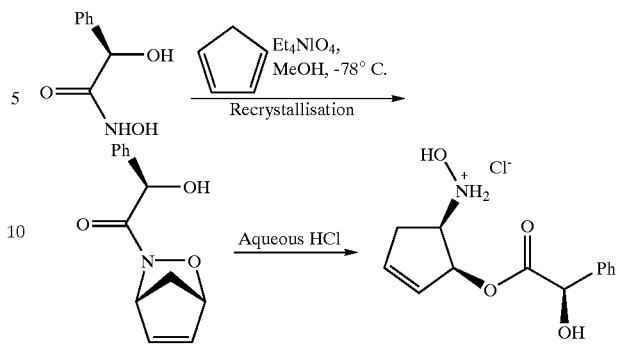

In the second route, Mulvihill et al. (*J. Org. Chem.*, 1998, 63, 3357–3363) employed a four-step sequence from cyclopentadiene, comprising acyl-nitroso cycloaddition, N—O bond scission, bioresolution and rearrangement of functional groups. The requirement for excess $Mo(CO)_6$ in the second step renders the overall approach unscaleable.

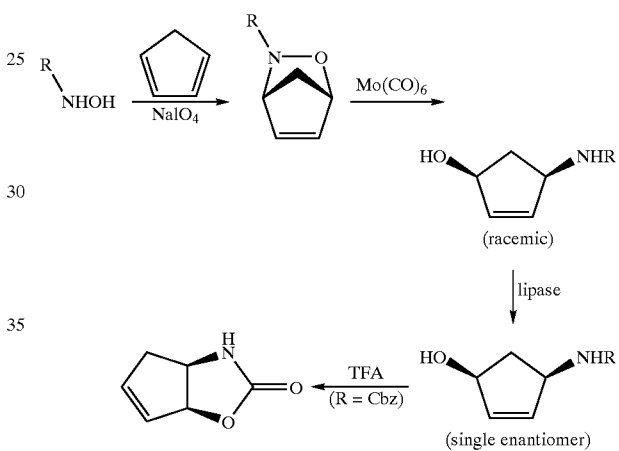

The carbocyclic nucleoside abacavir, a potent reverse transcriptase inhibitor, is synthesised using enantiomerically pure 2-azabicyclo[2.2.1]hept-5-en-3-one as a chiral building block. This drug has been produced at multi-tonne scale, and an economical bioresolution of 2-azabicyclo[2.2.1]hept-5-en-3-one has been developed to provide the chiral building block as a single enantiomer (WO-A-98/10075). This uses a cloned lactamase at high volume efficiency:

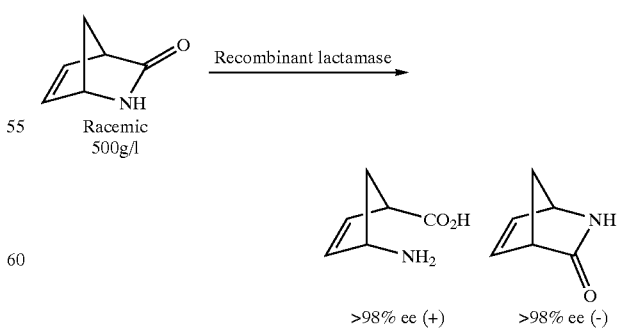

Both the residual lactam and the product amino acid can be converted into compounds of the following structures (2 & 3) using standard chemical methods.

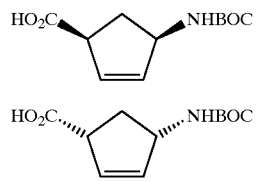

Maier et al (Synlett, August. 1998, 891–3) disclose the synthesis of cyclohexenylaminesby ring-closing metathesis. Oneproductofsuch reaction is further reacted as follows

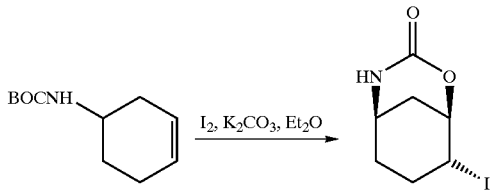

SUMMARY OF THE INVENTION

This invention is based on the discovery of an economical and convenient process to the cyclic carbamate 1. This process can be operated at scale, to access single enantiomer forms of 1 from starting materials 2 and 3 which are readily available in quantity via bioresolution of 2-azabicyclo[2.2.1] hept-5-en-3-one, and of which the simplest embodiment may be represented as follows:

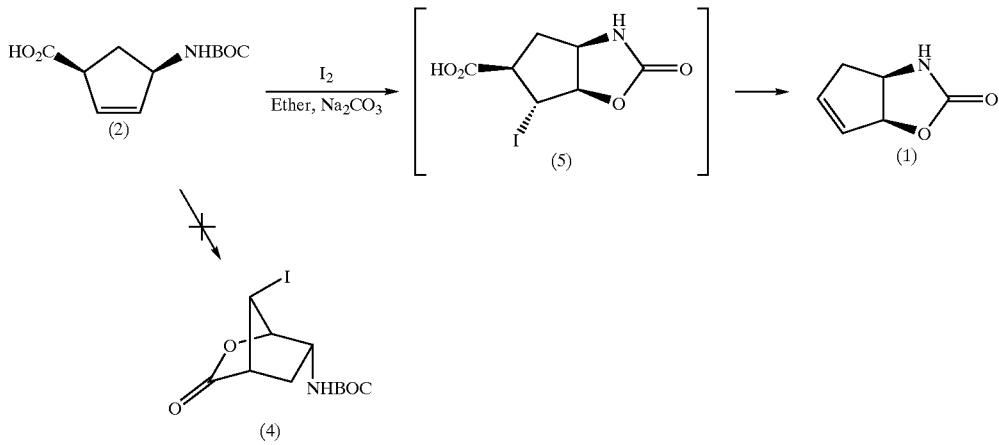

Halolactonisation of unsaturated carboxylic acids or their salts with iodine to form lactones has been known for several decades, and is a well-understood process. It was surprising that, when the cyclopentene carboxylic acid 2 was treated with iodine in a biphasic system of diethyl ether and saturated sodium bicarbonate, the expected γ-lactone 4 was not formed. Instead, the NHBoc function cyclises onto the adjacent carbon, to generate a putative intermediate 5 which undergoes decarboxylative elimination under the mildly basic conditions to give compound 1. The latter is obtained directly in high chemical purity. This is a scaleable reaction, and represents a superior route to the routes described above.

Instead of iodine, another halogen may be used. If required, a different carbamate protecting group can be used instead of N-Boc in the process of the present invention. The process may also be applied to N-substituted derivatives containing N—$R^1$ instead of N—H, $R^1$ being an organic group (alkyl, aryl, aralkyl etc, optionally substituted) of up to 20 C atoms. Also, the $CO_2H$ group may instead be $CO_2R^2$, $R^2$ being H, $C_{1-10}$ alkyl, aralkyl or aryl, e.g. of up to 10 C atoms.

DETAILED DESCRIPTION OF THE INVENTION

In a preferred embodiment, the base is an aqueous alkaline base, preferably aqueous sodium carbonate, and the reaction is conducted in a biphasic system. Preferably, enantiomerically enriched carbamate 1 of at least 80% ee, and more preferably at least 95% ee, is prepared.

If not already protected, the product may be converted, by known means, to a protected, e.g. the N-Boc, derivative. This is then ready for processing to a desired final product.

The following Examples illustrate the invention.

EXAMPLE 1

N-Boc-(+)-cis-3-amino-4-cyclopentene-1-carboxylic Acid

Methanol (300 ml) and 60 g (0.465 mol) (+)-cis-3-amino-4-cyclopentenecarboxylic acid (obtained from the bioresolution of 2-azabicyclo[2.2.1]hept-5-en-3-one) were stirred together, then 194 ml (1.39 mol) triethylamine slowly added. The reaction was cooled to 8° C. with ice, then 99 g (0.45 mol) di-t-butyl dicarbonate dissolved in 400 ml methanol was slowly added. After stirring for 48 hrs at ambient temperature the reaction was concentrated under reduced pressure to 100 ml and acidified to pH 3 with 1M $KHSO_4$. The solution was extracted twice with an equal volume of methyl t-butyl ether, the organic layer dried with $MgSO_4$, then evaporated under reduced pressure to give an off-white solid. This was recrystallised from a mixture of methyl t-butyl ether and heptane to give 90 g of N-Boc (+)-amino acid whose structure was verified by proton NMR.

EXAMPLE 2

3,3a,4,6a-Tetrahydrocyclopentaoxazol-2-one

Into a 100 ml round bottom flask were placed 1.5 g (6.6 mmol) of N-Boc (+)-amino acid, 7 ml of diethyl ether and 30 ml of saturated sodium bicarbonate solution. The resulting solution was cooled to 0° C. with an ice bath and a solution of 5.03 g (20 mmol) of iodine in 20 ml of THF was slowly added. After the addition was complete, the flask was protected from light with tin foil and left stirring at 0° C. overnight. The reaction was quenched with sodium sulfite solution and diluted with 10 ml saturated sodium bicarbonate solution. The solution was extracted with 3×30 ml dichloromethane and the combined organic extracts dried over magnesium sulfate. Solvent was removed by rotary evaporator to yield 208 mg of an off-white solid. Analysis by GC-MS showed a single component with a retention time of 14.82 minutes: m/z: 125 (M$^+$), 96, 80.

NMR (CDCl$_3$): 6.5 (1H, s, NH), 6.15–6.00 (1H, m), 5.95–5.75 (1H, m), 5.56 (1H, d, J=7.1), 4.45 (1H, t, J=6.6), 2.8–2.2 (2H, m).

What is claimed is:

1. A process for the preparation of a cyclic carbamate of formula (1), which comprises treatment of a cyclopentene of formula (2)

wherein R$^1$ is H or an organic group selected from the group consisting of substituted or unsubstituted C$_{1-20}$ alkyl, C$_{1-20}$ aryl, and C$_{1-20}$ aralkyl groups, and R$^2$ is C$_{1-10}$ alkyl, aralkyl or aryl, with a source of halogen and a base.

2. The process according to claim 1, wherein R$^1$ is H.

3. The process according to claim 1, wherein R$^2$ is tert-butyl.

4. The process according to claim 1, wherein said source of halogen is iodine.

5. The process according to claim 1, wherein said base is an aqueous base, and the reaction is conducted in a biphasic system.

6. The process according to claim 5, wherein said base is sodium carbonate.

7. The process according to claim 1, wherein enantiomerically enriched carbamate 1 of at least 80% ee is prepared.

8. The process according to claim 7, wherein enantiomerically enriched carbamate 1 of at least 95% ee is prepared.

9. The process according to claim 1, which further comprises conversion of compound 1 to the N-Boc derivative.

10. The process according to claim 1, wherein R$^1$ is an organic group selected from the group consisting of substituted or unsubstituted C$_{1-20}$ alkyl, C$_{1-20}$ aryl, and C$_{1-20}$ aralkyl groups.

11. The process according to claim 1, wherein R$^2$ is C$_{1-10}$ alkyl, aralkyl or aryl.

12. The process according to claim 11, wherein R$^2$ is C$_{1-10}$ alkyl.

13. The process according to claim 11, wherein R$^2$ is tert-butyl.

14. The process according to claim 11, wherein R$^2$ is an aralkyl group.

15. The process according to claim 11, wherein R$^2$ is an aryl group.

16. The process according to claim 2, wherein R$^2$ is tert-butyl.

17. The process according to claim 3, wherein said source of halogen is iodine, bromine, fluorine, or chlorine.

18. The process according to claim 3, wherein said source of halogen is iodine.

19. The process according to claim 11, wherein said source of halogen is iodine, bromine, fluorine, or chlorine.

20. The process according to claim 11, wherein said source of halogen is iodine.

21. The process according to claim 5, wherein said biphasic system comprises organic and aqueous solvents.

* * * * *